(12) United States Patent
Bachmann et al.

(10) Patent No.: US 9,572,918 B2
(45) Date of Patent: Feb. 21, 2017

(54) GRAPHENE-BASED FILTER FOR ISOLATING A SUBSTANCE FROM BLOOD

(71) Applicant: Lockheed Martin Corporation, Bethesda, MD (US)

(72) Inventors: Svetlana Monakhova Bachmann, Liverpool, NY (US); Paul Declan Mountcastle, Moorestown, NJ (US); Byron W. Tietjen, Baldwinsville, NY (US)

(73) Assignee: LOCKHEED MARTIN CORPORATION, Bethesda, MD (US)

( * ) Notice: Subject to any disclaimer, the term of this patent is extended or adjusted under 35 U.S.C. 154(b) by 522 days.

(21) Appl. No.: 13/923,503

(22) Filed: Jun. 21, 2013

(65) Prior Publication Data
US 2014/0377738 A1    Dec. 25, 2014

(51) Int. Cl.
*A61M 1/34* (2006.01)
*B01D 61/02* (2006.01)
(Continued)

(52) U.S. Cl.
CPC .............. *A61M 1/34* (2013.01); *A61K 35/14* (2013.01); *A61M 1/1631* (2014.02);
(Continued)

(58) Field of Classification Search
CPC ....... A61K 35/14; A61M 1/1631; A61M 1/34; A61M 1/165; A61M 1/1645; B01D 69/02;
(Continued)

(56) References Cited

U.S. PATENT DOCUMENTS

| | | | |
|---|---|---|---|
| 3,593,854 | A | 7/1971 | Swank |
| 3,701,433 | A | 10/1972 | Krakauer et al. |

(Continued)

FOREIGN PATENT DOCUMENTS

| | | |
|---|---|---|
| CN | 102423272 | 4/2012 |
| EP | 1 872 812 | 1/2008 |

(Continued)

OTHER PUBLICATIONS

Agenor et al. (2009), "Renal tubular dysfunction in human visceral leishmaniasis (Kala-azar)," Clinical nephrology 71. 5 (May 2009): 492-500.

(Continued)

*Primary Examiner* — John Kim
(74) *Attorney, Agent, or Firm* — Foley & Lardner LLP

(57) ABSTRACT

A device isolates a substance from blood. The substance includes particles with an effective diameter that is within a range defined by effective diameters of constituents of blood. The device comprises a first sheet of graphene including a first plurality of apertures. The first plurality of apertures are configured to pass objects with an effective diameter less than or equal to the effective diameter of the particles of the substance. The device comprises a second sheet of graphene including a second plurality of apertures. The second plurality of apertures are configured to pass objects with an effective diameter less than the effective diameter of the particles of the substance. The device may be configured to include a conduit system. The device may be configured to operate according to a reversible cycle.

27 Claims, 6 Drawing Sheets

(51) Int. Cl.
| | |
|---|---|
| *B01D 71/02* | (2006.01) |
| *A61K 35/14* | (2015.01) |
| *A61M 1/16* | (2006.01) |
| *B01D 69/02* | (2006.01) |
| *B01D 69/12* | (2006.01) |

(52) U.S. Cl.
CPC .............. *B01D 61/02* (2013.01); *B01D 69/02* (2013.01); *B01D 69/12* (2013.01); *B01D 71/021* (2013.01)

(58) Field of Classification Search
CPC ...... B01D 69/12; B01D 71/021; B01D 61/18; B01D 61/22; B01D 61/28; B01D 61/32; B01D 61/02
See application file for complete search history.

(56) References Cited

U.S. PATENT DOCUMENTS

| | | | |
|---|---|---|---|
| 4,073,732 A | 2/1978 | Lauer et al. | |
| 4,162,220 A | 7/1979 | Servas | |
| 4,303,530 A | 12/1981 | Shah et al. | |
| 4,743,371 A | 5/1988 | Servas et al. | |
| 4,925,560 A | 5/1990 | Sorrick | |
| 4,976,858 A | 12/1990 | Kadoya | |
| 5,080,770 A | 1/1992 | Culkin | |
| 5,185,086 A | 2/1993 | Kaali et al. | |
| 5,425,858 A | 6/1995 | Farmer | |
| 5,636,437 A | 6/1997 | Kaschmitter et al. | |
| 5,731,360 A | 3/1998 | Pekala et al. | |
| 5,902,762 A | 5/1999 | Mercuri et al. | |
| 5,932,185 A | 8/1999 | Pekala et al. | |
| 5,954,937 A | 9/1999 | Farmer | |
| 5,980,718 A | 11/1999 | Van Konynenburg et al. | |
| 6,309,532 B1 | 10/2001 | Tran et al. | |
| 6,346,187 B1 | 2/2002 | Tran et al. | |
| 6,462,935 B1 | 10/2002 | Shiue et al. | |
| 6,580,598 B2 | 6/2003 | Shiue et al. | |
| 6,659,298 B2 | 12/2003 | Wong | |
| 6,660,150 B2 | 12/2003 | Conlan et al. | |
| 6,661,643 B2 | 12/2003 | Shiue et al. | |
| 7,014,829 B2 | 3/2006 | Yanagisawa et al. | |
| 7,138,042 B2 | 11/2006 | Tran et al. | |
| 7,175,783 B2 | 2/2007 | Curran | |
| 7,267,753 B2 | 9/2007 | Anex et al. | |
| 7,374,677 B2 | 5/2008 | McLaughlin et al. | |
| 7,459,121 B2 | 12/2008 | Liang et al. | |
| 7,505,250 B2 | 3/2009 | Cho et al. | |
| 7,531,094 B2 | 5/2009 | McLaughlin et al. | |
| 7,600,567 B2 | 10/2009 | Christopher et al. | |
| 7,706,128 B2 | 4/2010 | Bourcier | |
| 7,761,809 B2 | 7/2010 | Bukovec et al. | |
| 8,109,893 B2 | 2/2012 | Lande | |
| 8,147,599 B2 | 4/2012 | McAlister | |
| 8,361,321 B2 | 1/2013 | Stetson et al. | |
| 9,028,663 B2 | 5/2015 | Stetson et al. | |
| 9,067,811 B1 | 6/2015 | Bennett et al. | |
| 9,095,823 B2 | 8/2015 | Fleming | |
| 9,193,587 B2 | 11/2015 | Bennett et al. | |
| 2004/0199243 A1* | 10/2004 | Yodfat ...................... A61F 2/01 623/1.16 | |
| 2005/0189673 A1 | 9/2005 | Klug et al. | |
| 2006/0121279 A1 | 6/2006 | Petrik | |
| 2006/0151382 A1 | 7/2006 | Petrik | |
| 2009/0294300 A1 | 12/2009 | Kanzius | |
| 2010/0016778 A1 | 1/2010 | Chattopadhyay | |
| 2010/0025330 A1 | 2/2010 | Ratto et al. | |
| 2010/0127312 A1 | 5/2010 | Grebel et al. | |
| 2010/0167551 A1 | 7/2010 | DeDontney | |
| 2012/0048804 A1* | 3/2012 | Stetson ................. B01D 61/02 210/653 | |
| 2012/0183738 A1 | 7/2012 | Zettl et al. | |
| 2012/0211367 A1* | 8/2012 | Vecitis ................. B82Y 30/00 204/554 | |
| 2012/0255899 A1 | 10/2012 | Choi et al. | |
| 2013/0015136 A1 | 1/2013 | Bennett et al. | |
| 2013/0105417 A1 | 5/2013 | Stetson et al. | |
| 2013/0240355 A1 | 9/2013 | Ho et al. | |
| 2013/0248367 A1* | 9/2013 | Stetson, Jr. ........... B01D 57/02 204/518 | |
| 2013/0249147 A1 | 9/2013 | Bedworth | |
| 2013/0256210 A1 | 10/2013 | Fleming | |
| 2013/0256211 A1 | 10/2013 | Fleming | |
| 2013/0277305 A1 | 10/2013 | Stetson et al. | |
| 2014/0261999 A1 | 9/2014 | Stetson et al. | |
| 2014/0263035 A1 | 9/2014 | Stoltenberg et al. | |
| 2014/0263178 A1 | 9/2014 | Sinton et al. | |
| 2014/0272286 A1 | 9/2014 | Stoltenberg et al. | |
| 2015/0075667 A1 | 3/2015 | McHugh et al. | |
| 2015/0217219 A1 | 8/2015 | Sinsabaugh et al. | |
| 2015/0218210 A1 | 8/2015 | Stetson et al. | |
| 2015/0221474 A1 | 8/2015 | Bedworth et al. | |
| 2015/0247178 A1 | 9/2015 | Mountcastle et al. | |
| 2015/0258254 A1 | 9/2015 | Simon et al. | |
| 2015/0258498 A1 | 9/2015 | Simon et al. | |
| 2015/0258502 A1 | 9/2015 | Turowski et al. | |
| 2015/0258503 A1 | 9/2015 | Sinton et al. | |
| 2015/0258525 A1 | 9/2015 | Westman et al. | |
| 2015/0268150 A1 | 9/2015 | Newkirk et al. | |
| 2015/0321147 A1 | 11/2015 | Fleming et al. | |
| 2015/0336202 A1 | 11/2015 | Bedworth et al. | |
| 2016/0009049 A1 | 1/2016 | Stoltenberg et al. | |

FOREIGN PATENT DOCUMENTS

| | | |
|---|---|---|
| EP | 1 603 609 | 5/2011 |
| EP | 2 511 002 | 10/2012 |
| EP | 2 586 473 | 5/2013 |
| KR | 1020120022164 | 3/2012 |
| WO | WO 2004/082733 | 9/2004 |
| WO | WO 2012/006657 | 1/2012 |
| WO | WO 2012/030368 | 3/2012 |
| WO | WO 2013/138137 | 9/2013 |

OTHER PUBLICATIONS

Albert et al. (2009), "Ringer's lactate is compatible with the rapid infusion of AS-3 preserved packed red blood cells," Canadian journal of anaesthesia = Journal canadien d'anesthésie 56. 5 (May 2009): 352-6.

Aso et al. (2006), "Comparison of serum high-molecular weight (HMW) adiponectin with total adiponectin concentrations in type 2 diabetic patients with coronary artery disease using a novel enzyme-linked immunosorbent assay to detect HMW adiponectin," Diabetes 55. 7 (Jul. 2006): 1954-60.

Axelsson et al. (2010), "Acute hyperglycemia induces rapid, reversible increases in glomerular permeability in nondiabetic rats," American journal of physiology. Renal physiology 298. 6 (Jun. 2010): F1306-12.

Bae et al. (Jun. 20, 2010) "Roll-to-roll production of 30-inch graphene films for transparent electrodes," *Nature Nanotechnology.* 5:574-578.

Bains et al. (2005), "Novel lectins from rhizomes of two *Acorus* species with mitogenic activity and inhibitory potential towards murine cancer cell lines," international immunopharmacology 5. 9 (Aug. 2005): 1470-8.

Bazargani (2005), "Acute inflammation in peritoneal dialysis: experimental studies in rats. Characterization of regulatory mechanisms," Swedish dental journal. Supplement 171 (2005): 1-57, i.

Bazargani et al. (2005), "Low molecular weight heparin improves peritoneal ultrafiltration and blocks complement and coagulation," Peritoneal dialysis international : journal of the International Society for Peritoneal Dialysis 25. 4 (Jul. 2005-Aug. 2005): 394-404.

Beppu et al. (2006), "Antidiabetic effects of dietary administration of Aloe arborescens Miller components on multiple low-dose streptozotocin-induced diabetes in mice: investigation on hypoglycemic action and systemic absorption dynamics of aloe components," Journal of ethnopharmacology 103. 3 (Feb. 20, 2006): 468-77.

(56) References Cited

OTHER PUBLICATIONS

Cohen-Tanugi (Jun. 5, 2012) "Water Desalination across Nanoporous Graphene," *Nano Lett.* 12(7):3602-3608.

Deng et al. (2010), "Renal protection in chronic kidney disease: hypoxia-inducible factor activation vs. angiotensin II blockade," American journal of physiology. Renal physiology 299.6 (Dec. 2010): F1365-73.

Freedman et al. (2010), "Genetic basis of nondiabetic end-stage renal disease," Seminars in nephrology 30. 2 (Mar. 2010): 101-10.

García-López et al. (2005), "Determination of high and low molecular weight molecules of icodextrin in plasma and dialysate, using gel filtration chromatography, in peritoneal dialysis patients,"Peritoneal dialysis international : journal of the International Society for Peritoneal Dialysis 25. 2 (Mar. 2005-Apr. 2005): 181-91.

Gnudi (2008), "Molecular mechanisms of proteinuria in diabetes", Biochemical Society transactions 36. Pt 5 (Oct. 2008): 946-9.

Gotloib et al. (2005), "Peritoneal dialysis in refractory end-stage congestive heart failure: a challenge facing a no-win situation," Nephrology, dialysis, transplantation : official publication of the European Dialysis and Transplant Association—European Renal Association 207 (Jul. 2005): vii32-6.

Huang et al. (2010), "Gene expression profile in circulating mononuclear cells after exposure to ultrafine carbon particles," Inhalation toxicology 22. 10 (Aug. 2010): 835-46.

International Search Report and Written Opinion dated Sep. 30, 2014, for International Application No. PCT/US2014/041766.

Jiang et al. (Dec. 9, 2009) "Porous Graphene as the Ultimate Membrane for Gas Separation," *Nano Letters.* 9:4019-4024.

Jiao et al. (2009), "Castration differentially alters basal and leucine-stimulated tissue protein synthesis in skeletal muscle and adipose tissue," American journal of physiology. Endocrinology and metabolism 297. 5 (Nov. 2009): E1222-32.

Kang et al. (2009), "Effect of eplerenone, enalapril and their combination treatment on diabetic nephropathy in type II diabetic rats," Nephrology, dialysis, transplantation : official publication of the European Dialysis and Transplant Association—European Renal Association 24. 1 (Jan. 2009): 73-84.

Kar et al. (2006), "Effect of glycation of hemoglobin on its interaction with trifluoperazine," The protein journal 25. 3 (Apr. 2006): 202-11.

Karan et al. (Jan. 27, 2012) "Ultrafast Viscous Permeation of Organic Solvents Through Diamond-Like Carbon Nanosheets," *Science.* 335:444-447.

Kawamoto et al. (2010), "Serum high molecular weight adiponectin is associated with mild renal dysfunction in Japanese adults," Journal of atherosclerosis and thrombosis 17. 11 (Nov. 27, 2010): 1141-8.

Kim et al. (2010), "Fabrication and Characterization of Large Area, Semiconducting Nanoperforated Graphene Materials," Nano Letters 2010; vol. 10, No. 4, Mar. 1, 2010, pp. 1125-1131.

Kumar et al. (2005), "Modulation of alpha-crystallin chaperone activity in diabetic rat lens by curcumin," Molecular vision 11 (Jul. 26, 2005): 561-8.

Liu et al. (Jun. 9, 2008) "Graphene Oxidation: Thickness-Dependent Etching and Strong Chemical Doping," *Nano Letters.* 2008 8:1965-1970.

Mishra et al. (Jan. 13, 2011) "Functionalized Graphene Sheets For Arsenic Removal And Desalination Of Sea Water," *Desalination.* 282:39-45.

Morse (Apr. 30, 2010) Review of Kim et al. (Mar. 1, 2010) "Fabrication and Characterization of Large-Area, Semiconducting Nanoperforated Graphene Materials," *InterNano Resources for Nanomanufacturing*.

Nair et al. (Jan. 27, 2012) "Unimpeded Permeation of Water Through Helium-Leak-tight Graphene-Based Membranes," *Science.* 335:442-443.

*Nanoporous Graphene Could Outperform Best Commercial Water Desalination Techniques;* Tanugi & Grossman; ACS 20 12; Jun. 25, 2012; Weftec 2012; Sep. 29-Oct. 3.

Nezlin (2009), "Circulating non-immune IgG complexes in health and disease," Immunology letters 122. 2 (Feb. 21, 2009): 141-4.

Norata et al. (2010), "Plasma adiponectin levels in chronic kidney disease patients: relation with molecular inflammatory profile and metabolic status," Nutrition, metabolism, and cardiovascular diseases : NMCD 20. 1 (Jan. 2010): 56-63.

Ogawa et al. (2008), "Exosome-like vesicles in Gloydius blomhoffii blomhoffii venom," Toxicon : official journal of the International Society on Toxinology 51. 6 (May 2008): 984-93.

Oki et al. (2009), "Combined acromegaly and subclinical Cushing disease related to high-molecular-weight adrenocorticotropic hormone," Journal of neurosurgery 110. 2 (Feb. 2009): 369-73.

Osorio et al. (2009), "Effect of treatment with losartan on salt sensitivity and SGLT2 expression in hypertensive diabetic rats," Diabetes research and clinical practice 86. 3 (Dec. 2009): e46-9.

Osorio et al. (2010), "Effect of phlorizin on SGLT2 expression in the kidney of diabetic rats,"Journal of nephrology 23. 5 (Sep. 2010-Oct. 2010): 541-6.

Padidela et al. (2009), "Elevated basal and post-feed glucagon-like peptide 1 (GLP-1) concentrations in the neonatal period," European journal of endocrinology / European Federation of Endocrine Societies 160. 1 (Jan. 2009): 53-8.

Paul (Jan. 27, 2012) "Creating New Types of Carbon-Based Membranes," *Science.* 335:413-414.

Ribeiro et al. (2006), "Binary Mutual Diffusion Coefficients of Aqueous Solutions of Sucrose, Lactose, Glucose, and Fructose in the Temperature Range from (298.15 to 328.15) K," Journal of Chemical and Engineering Data, vol. 51, No. 5.

Rippe et al. (2007), "Size and charge selectivity of the glomerular filter in early experimental diabetes in rats," American journal of physiology. Renal physiology 293. 5 (Nov. 2007): F1533-8.

Sethna et al. (2009), "Serum adiponectin levels and ambulatory blood pressure monitoring in pediatric renal transplant recipients," Transplantation 88. 8 (Oct. 27, 2009): 1030-7.

Sint et al. (Nov. 14, 2008) "Selective Ion Passage through Functionalized Graphene Nanopores," *J. Am. Chem. Soc.* 130(49):16448-16449.

Suk et al. (Apr. 30, 2010) "Water Transport Through Ultrathin Graphene," *Journal of Physical Chemistry Letters.* 1(10):1590-1594.

Sullivan et al. (2005), "Microarray analysis reveals novel gene expression changes associated with erectile dysfunction in diabetic rats," Physiological genomics 23. 2 (Oct. 17, 2005): 192-205.

Takata et al. (2008), "Hyperresistinemia is associated with coexistence of hypertension and type 2 diabetes," Hypertension 51. 2 (Feb. 2008): 534-9.

Tamborlane et al. (2008), "Continuous Glucose Monitoring and Intensive Treatment of Type 1 Diabetes"; N Engl J Med 359;14: 1464-1476.

Totani et al. (2008), "Gluten binds cytotoxic compounds generated in heated frying oil," Journal of oleo science 57. 12 (2008): 683-90.

Tsukamoto et al. (2008), "Purification, characterization and biological activities of a garlic oligosaccharide," Journal of UOEH 30. 2 (Jun. 1, 2008): 147-57.

Vallon (2009), "Micropuncturing the nephron," Pflügers Archiv : European journal of physiology 458. 1 (May 2009): 189-201.

Vriens et al. (2010), "Methodological considerations in quantification of oncological FDG PET studies," European journal of nuclear medicine and molecular imaging 37. 7 (Jul. 2010): 1408-25.

Wang et al. (2008), "What is the role of the second "structural" NADP+-binding site in human glucose 6-phosphate dehydrogenase?,"Protein science : a publication of the Protein Society 17.8 (Aug. 2008): 1403-11.

Xie et al. (2008), "Fractionation and characterization of biologically-active polysaccharides from Artemisia tripartite," Phytochemistry 69. 6 (Apr. 2008): 1359-71.

Yagil et al. (2005), "Nonproteinuric diabetes-associated nephropathy in the Cohen rat model of type 2 diabetes," Diabetes 54. 5 (May 2005): 1487-96.

Zhang et al. (2007), "Isolation and activity of an alpha-amylase inhibitor from white kidney beans," Yao xue xue bao = Acta pharmaceutica Sinica 42. 12 (Dec. 2007): 1282-7.

(56) References Cited

OTHER PUBLICATIONS

Zhu et al. (2011), "Carbon Nanotubes in Biomedicine and Biosensing," in Carbon Nanotubes—Growth and Applications, Ch. 6, pp. 135-162.
Ziegelmeier et al. (2008), "Adipokines influencing metabolic and cardiovascular disease are differentially regulated in maintenance hemodialysis," Metabolism: clinical and experimental 57. 10 (Oct. 2008): 1414-21.
Zirk et al. (2007), "A refractometry-based glucose analysis of body fluids," Medical engineering & physics 29. 4 (May 2007): 449-58.
U.S. Appl. No. 14/754,531, filed Jun. 29, 2015.
U.S. Appl. No. 14/856,198, filed Sep. 16, 2015.
U.S. Appl. No. 14/856,471, filed Sep. 16, 2015.
U.S. Appl. No. 14/843,944, filed Sep. 2, 2015.

\* cited by examiner

GRAPHENE-BASED FILTER FOR ISOLATING A SUBSTANCE FROM BLOOD

TECHNICAL FIELD

This disclosure relates to systems and methods for isolating a substance from a solution. In particular, this disclosure describes systems and methods for using multiple graphene-based filters to isolate a substance from blood.

BACKGROUND

Blood includes several constituents ranging in size. For example, hemoglobin has an effective molecular radius of 3.25 nanometers (nm) and sodium has an effective molecular radius of 0.10 nm. Substances having particles with a size within the range of blood constituents may be harmful when they are dissolved or suspended in blood. For example, certain viruses and toxics are sized within the range of constituents of blood. Further, some individuals may have conditions that lead to elevated amounts of regularly occurring constituents. Elevated amounts of regularly occurring blood constituents may be unhealthy to individuals. For example, diabetes is a metabolic disease that may lead to elevated levels of glucose. Elevated levels of glucose may lead to serious complications, such as organ failure.

In order to control blood sugar levels, diabetics may follow a strict diet regimen or inject insulin. However, insulin injections do not literally remove sugar from the blood. Insulin opens cell walls to allow glucose to enter where it is converted to glycogen and fat. Thus, insulin injections may lead to obesity, which may aggravate diabetes and increase the risk of other diseases, such as heart disease, colon cancer, and hypertension.

SUMMARY

In general, this disclosure relates to systems and methods for isolating a substance from a solution. In particular, this disclosure describes systems and methods for using multiple graphene-based filters to isolate a substance having particles sized within the constituents of blood from a bloodstream. The substance may be a constituent of blood occurring at an elevated level or a foreign substance. The techniques of this disclosure may be used for the treatment of diseases, such as, for example diabetes. In one example, the techniques of this disclosure may be applied to remove excess glucose from the blood. The techniques of this disclosure may allow for non-hormonal glucose control, thereby preventing excess glucose from being converted to glycogen and fat. Although the techniques of this disclosure are described with respect to blood and example substances, the techniques of this disclosure may be generally applied to isolating particles or molecules of one species from a solution or suspension containing both larger and smaller particles or molecules.

According to one example of this disclosure a device for isolating a substance from blood, wherein particles of the substance have an effective diameter that is within a range defined by effective diameters of constituents of blood, the device comprises a first sheet of graphene including a first plurality of apertures, wherein the first plurality of apertures are configured to pass objects with an effective diameter less than or equal to the effective diameter of the particles of the substance, a second sheet of graphene including a second plurality of apertures, wherein the second plurality of apertures are configured to pass objects with an effective diameter less than the effective diameter of the particles of the substance, and a conduit system coupled to the first sheet of graphene and the second sheet of graphene, wherein the conduit system is configured to isolate the particles of the substance as blood flows through the conduit system.

According to one example of this disclosure a device for isolating a substance from blood, wherein particles of the substance have an effective diameter that is within a range defined by effective diameters of constituents of blood, comprises a first sheet of graphene including a first plurality of apertures, wherein the first plurality of apertures are configured to pass objects with an effective diameter less than or equal to the effective diameter of the particles of the substance, a second sheet of graphene including a second plurality of apertures, wherein the second plurality of apertures are configured to pass objects with an effective diameter less than the effective diameter of the particles of the substance, and a mechanical system coupled to the first sheet of graphene and the second sheet of graphene, wherein the mechanical system is configured to isolate the particles of the substance using a reversible cycle.

According to one example of the disclosure, a method for isolating a substance from blood, wherein particles of the substance have an effective diameter that is within a range defined by effective diameters of constituents of blood, comprises regulating the flow of the blood through a first sheet of graphene including a first plurality of apertures, wherein the first plurality of apertures are configured to pass objects with an effective diameter less than or equal to the effective diameter of the particles of the substance, and regulating the flow of the blood through a second sheet of graphene including a second plurality of apertures, wherein the second plurality of apertures are configured to pass molecules with an effective diameter less than the effective diameter of the particles of the substance.

According to another example of the disclosure an apparatus configured to isolate a substance from blood, wherein particles of the substance have an effective diameter that is within a range defined by effective diameters of constituents of blood, comprises means for regulating the flow of the blood through a first sheet of graphene including a first plurality of apertures, wherein the first plurality of apertures are configured to pass objects with an effective diameter less than or equal to the effective diameter of the particles of the substance, and means for regulating the flow of the blood through a second sheet of graphene including a second plurality of apertures, wherein the second plurality of apertures are configured to pass molecules with an effective diameter less than the effective diameter of the particles of the substance.

The details of one or more examples are set forth in the accompanying drawings and the description below. Other features, objects, and advantages will be apparent from the description and drawings, and from the claims.

BRIEF DESCRIPTION OF DRAWINGS

This written disclosure describes illustrative embodiments that are non-limiting and non-exhaustive. Reference is made to illustrative embodiments that are depicted in the figures, in which.

DETAILED DESCRIPTION

Figure 1:
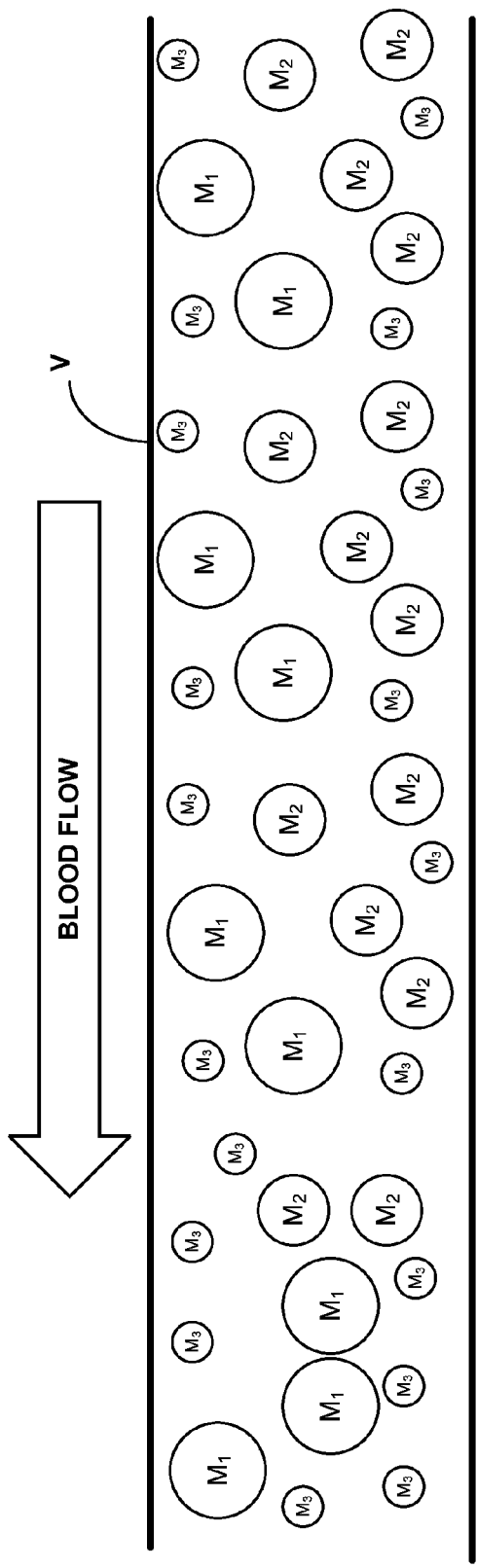
FIG. 1 is a conceptual diagram illustrating substances dissolved or suspended in the blood stream.

Molecular filtration techniques are emerging due to nanotechnology developments. Commonly assigned U.S. Pat. No. 8,361,321 (hereinafter "Stetson"), which is incorporated herein by reference in its entirety, describes using a graphene sheet with nano-sized perforations to remove unwanted ions from water. While a single graphene sheet with nano-sized perforations can be used to separate larger molecules from smaller molecules, filtration techniques that use a single molecular membrane with one perforation size may be not be able to selectively isolate an object of a particular size from objects within a band of sizes. Because blood has several regularly occurring constituents of varying sizes, filtration techniques using a single graphene sheet may not be able to remove a substance without also removing regularly occurring constituents. In the United States, 5.8 million people or 8.3% of the population suffer from diabetes. Diabetes can be treated by removing excess glucose from the bloodstream. Because glucose is sized between other constituents of blood, removing glucose from blood using a single filter may not be an effective treatment because the filter may also remove other "healthy" blood constituents. The systems and techniques described herein provide techniques for isolating particles of a substance from blood where the particles are sized within the size of the constituents of blood, such as, e.g., glucose. The systems and techniques described herein may provide effective non-hormonal treatments to diseases, such as e.g., diabetes.

Although the techniques of this disclosure are described in the examples below with respect to blood and glucose, the techniques of this disclosure may be generally applied to isolating particles or molecules of one species from a solution or suspension containing both larger and smaller particles and/or molecules. Embodiments of the present disclosure may be best understood by reference to the drawings, wherein like parts are designated by like numerals throughout. It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In addition, the steps of a method do not necessarily need to be executed in any specific order, or even sequentially, nor need the steps be executed only once, unless otherwise specified. In some cases, well-known structures, materials, or operations are not shown or described in detail.

Human blood typically includes 55% plasma. Plasma is composed of 90% water and dissolved substances (e.g., sodium, chlorine, potassium, manganese, and calcium ions). The remaining 10% of plasma is composed of blood plasma proteins (e.g., albumin, globulin, and fibrinogen) and hormones. The 45% of human blood that is not composed of plasma is typically composed of 99% erythrocytes (i.e., red cells), less than 1% leucocytes (i.e., white cells), and less than 1% thrombocytes (i.e., platelets). Table 1 illustrates the relative size of constituents of blood with respect to one another. Table 1 illustrates the permselectivity of blood constituents in the glomerulus. It should be noted that the actual sizes of constituents in Table 1 may vary based on several factors (e.g., temperature) and may be expressed in several different manners. In this manner, Table 1 should not be limiting.

TABLE 1

Constituents of Blood

| Substance | Molecular Mass (g/mol) | Effective molecular radius (nm) |
|---|---|---|
| sodium | 23 | 0.10 |
| potassium | 39 | 0.14 |
| water | 18 | 0.15 |
| urea | 60 | 0.16 |
| chloride | 35.5 | 0.18 |
| glucose | 180 | 0.33 |
| sucrose | 342 | 0.44 |
| polyethylene glycol | 1 | 0.70 |
| inulin | 5.2 | 1.48 |
| myoglobin | 16.9 | 1.88 |
| lysozyme | 14.6 | 1.90 |
| lactoglobulin | 36 | 2.16 |
| egg albumin | 43.5 | 2.80 |
| hemoglobin | 68 | 3.25 |
| serum albumin | 69 | 3.55 |

This disclosure describes examples where glucose is isolated from blood. As illustrated in Table 1, glucose is physically smaller than dissolved proteins, but larger than mineral ions that are the major constituents of blood plasma. Ribeiro et al "Binary Mutual Diffusion Coefficients of Aqueous Solutions of Sucrose, Lactose, Glucose, and Fructose in the Temperature Range from (298.15 to 328.15) K," Journal of Chemical and Engineering Data, Vol. 51, No. 5, 2006, which is incorporated by reference, in its entirety, provides values for the effective hydrodynamic radius of glucose in an aqueous solution at different temperatures. Based on the values provided in Ribeiro, the examples below assume that the effective diameter of particles of glucose dissolved in blood at body temperature is approximately 0.72 nm. It should be noted that the systems and techniques described herein are not limited based on an assumed particle size of a substance. The examples below can readily be modified based on measured or predicted particle sizes. Further, the term effective diameter is used herein to describe the size of an object based on the diameter of a sphere that would encapsulate the object. It most cases the object may not actually have a spherical shape and the effective diameter may generally correspond to a length of an object.

FIG. 1 is a conceptual diagram illustrating substances dissolved or suspended in the bloodstream. In the example illustrated in FIG. 1, blood flows through vein V. In FIG. 1, $M_2$ represents particles of a substance to be isolated from the bloodstream and $M_1$ and $M_3$ respectively represent larger and smaller constituents of blood. For example, as describe above, $M_2$ may represent a dissolved glucose molecule with an effective diameter of 0.72 nm, $M_1$ may represent myoglobin with an effective diameter of 3.75 nm, and $M_3$ may represent urea with an effective diameter of 0.32 nm. In other examples, $M_2$ may be a bio-pathogen (a virus or a bacterium) or a toxin. Toxins may include, for example, heavy metals (e.g., lead) or alcohol. As described above, removing $M_2$ blood without also removing $M_1$ and $M_3$ may be difficult using conventional techniques. In some cases, removing $M_1$ or $M_3$ from a patient's bloodstream may result in more health consequences to the patient than simply leaving $M_2$ in the bloodstream.

Figure 2:
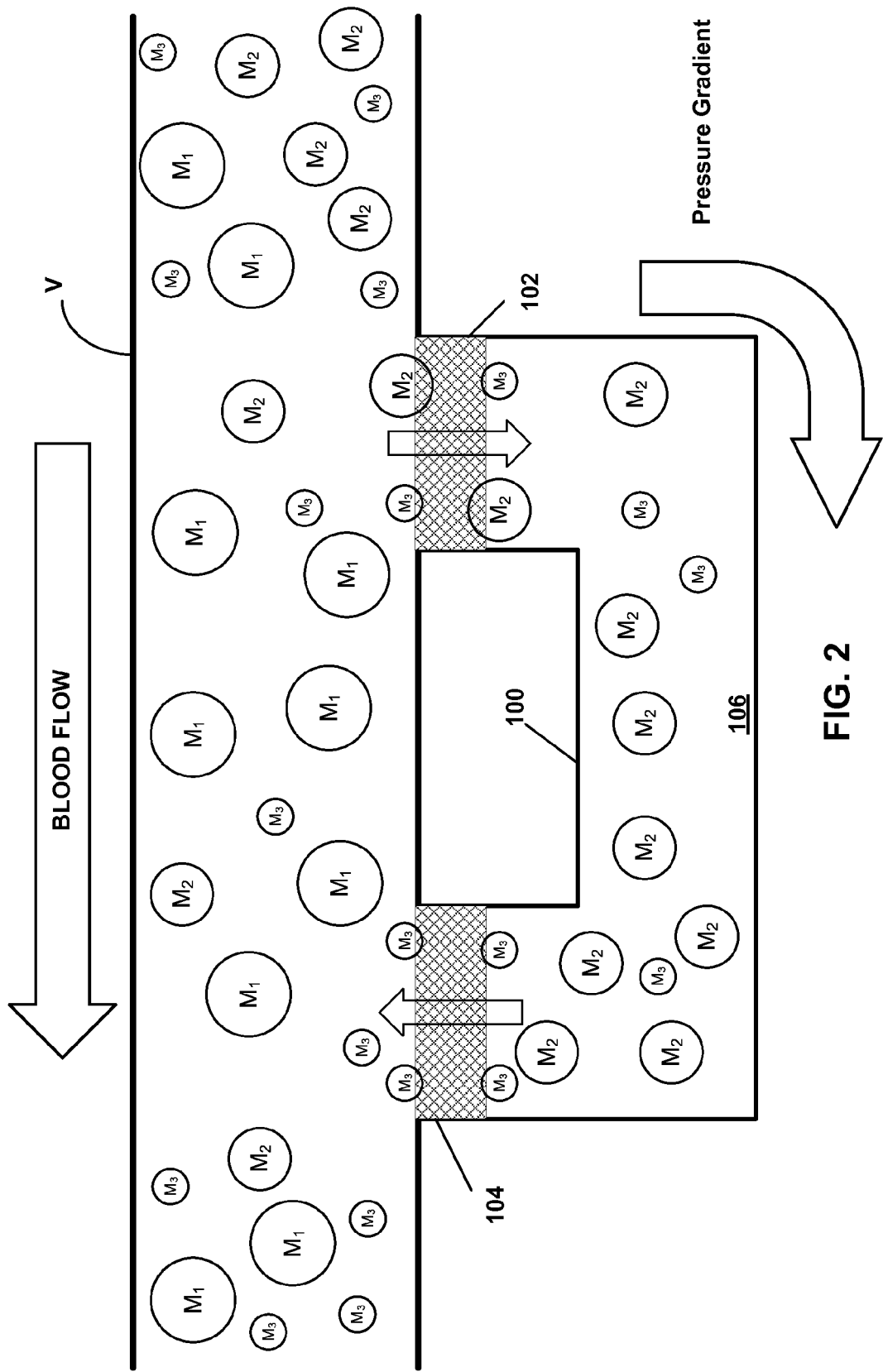
FIG. 2 is a conceptual diagram illustrating an example of two stage bypass filtering according to techniques described in this disclosure.

FIG. 2 is a conceptual diagram illustrating an example of two stage bypass filtering according to techniques described in this disclosure. The conceptual diagram illustrated in FIG. 2, illustrates an example where two stage filter 100 is configured to isolate a substance from blood. Similar to FIG. 1, particles of a substance to be isolated are illustrated as $M_2$, particles larger than $M_2$ are illustrated as $M_1$, and particles smaller than $M_2$ are illustrated as $M_3$. As illustrated in FIG. 2, two stage filter 100 is operably coupled to vein V. It should be noted that while two stage filter 100 is illustrated in FIG. 2 as being directly coupled to vein V, two stage filter 100 may be coupled to vein V using a series of one or more intermediate conduits. Further, it should be noted that while the example in FIG. 2 illustrates two stage filter 100 as being operably coupled to a vein, two stage filter 100 may be operably coupled to any part of the circulatory system (e.g., an artery).

Two stage filter 100 includes first filter 102, second filter 104, and conduit 106. Two stage filter 100 may be located outside of the body as a standalone device or may be part of an implantable medical device implanted in a patient. As illustrated in FIG. 2, as blood flows through vein V, pressure gradient causes blood to flow into conduit 106 and bypass the normal path through V. In some cases, the pressure gradient may be generated using a small pump or electromagnetic fields, thereby drawing blood into conduit 106. In other cases, the natural flow of blood through vein V and/or gravitation forces may be sufficient to cause blood to flow into conduit 106. First filter 102 is disposed at the proximal end of conduit 106. First filter 102 may be configured to pass only particles with a size less than or equal to the particles of the substance to be isolated from bloodstream. Thus, as illustrated in FIG. 2 particles larger than $M_2$, i.e., $M_1$, do not enter conduit 106. For example, if $M_2$ represents glucose particles and $M_1$ represents myoglobin particles, glucose particles and smaller particle will enter conduit 106 and myoglobin particles will continue to flow through vein V unabated. Second filter 104 is disposed at the distal end of conduit 106. Second filter 104 may be configured to only allow passage of particles with a size less than particles $M_2$, i.e., $M_3$. Thus, the particles smaller than $M_2$ that have entered conduit 106 will return to vein V, while $M_2$ particles remain in conduit 106. In this manner, $M_2$ particles are effectively isolated from the bloodstream.

As blood continues to flow through vein V, $M_2$ particles may continue to enter conduit 106 and will accumulate. Two stage filter 100 may be configured such that $M_2$ particles may be removed from conduit 106. In some examples, conduit 106 may be configured to be decoupled from two stage filter 100. In other examples, conduit 106 may be coupled to one or more valves (not shown in FIG. 2) that may be opened to remove $M_2$ particles from conduit 106. In some cases, conduit 106 may become saturated with $M_2$ particles and $M_2$ particles may be siphoned off when saturation is achieved. The process of isolating $M_2$ particles in conduit 106 and removing $M_2$ particles from conduit 106 can be repeated, as desired.

It should be noted that in some cases, based on the pressure gradient and rate of blood flow, some $M_2$ and $M_3$ particles may continue to flow through vein V unabated without entering conduit 106. However, pressure gradient may be configured such that a desired percentage of $M_2$ and $M_3$ particles flow through first filter 102 and into conduit 106. Typically there is only 5 grams of glucose is in the bloodstream of a healthy 75 kg adult with 5 liters of blood. Thus, in the case where $M_2$ is glucose, pressure gradient and two stage filter 100 may be configured to produce a known rate of filtration in order to maintain a healthy level of glucose in the bloodstream.

As described above, first filter 102 may be configured to pass only particles with a size less than or equal to the particles of the substance to be isolated from bloodstream and second filter 104 may be configured to only allow passage of particles with a size less than particles of a substance to be isolated. In one example, first filter 102 and/or second filter 104 may be a sheet of graphene including a plurality of apertures, e.g., a perforated graphene sheet. Graphene is a single-atomic-layer-thick layer of carbon atoms which may form a sheet. The carbon atoms of a graphene sheet define a repeating pattern of hexagonal ring structures (benzene rings) constructed of six carbon atoms, which form a honeycomb lattice of carbon atoms. An interstitial aperture is formed by each six carbon atom ring structure in the sheet and this interstitial aperture is much less than one nanometer across and is much too small to allow the passage of water or other blood constituents. As described in publications Liu, Li et al., "Graphene Oxidation: Thickness-Dependent Etching and Strong Chemical Doping," Nano Letters 2008; vol. 8, No. 7, Jun. 9, 2008 pg 1965-1970 and Kim et al "Fabrication and Characterization of Large Area, Semiconducting Nanoperforated Graphene Materials," Nano Letters 2010; vol. 10, No. 4, Mar. 1, 2010, pp 1125-1131, (each of which are incorporated by reference in their entirety) perforations can be made on a sheet of graphene. Perforene™ is an example trade name of a perforated graphene sheet. The techniques of this disclosure are not limited to particular techniques for making perforations on graphene and any technique, such as laser drilling, may be used to introduce perforations on a graphene sheet in accordance with the techniques described herein.

Figure 3:
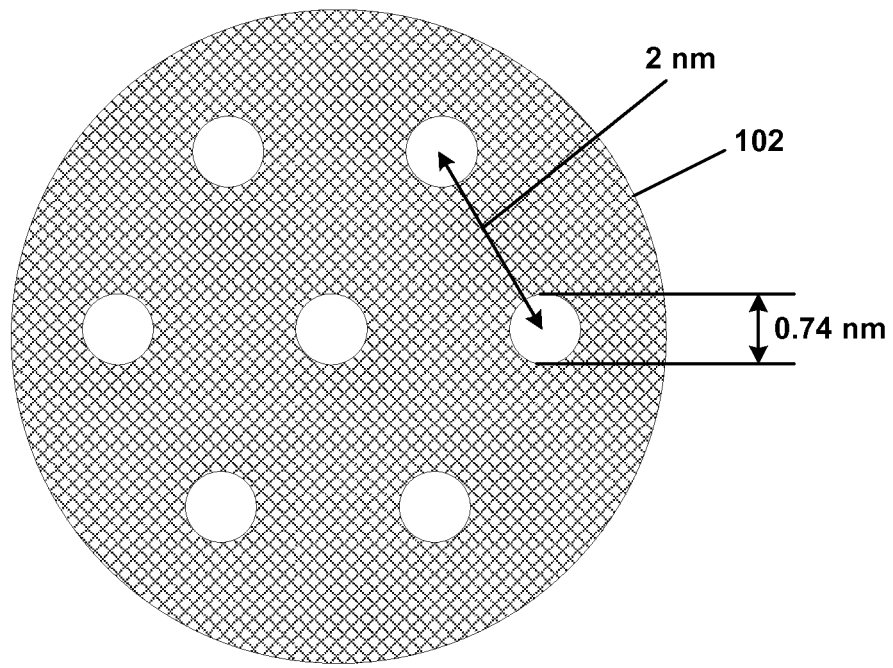
FIG. 3 is a conceptual diagram illustrating a cross-sectional view of a filter according to techniques of this disclosure.

FIG. 3 is a conceptual diagram illustrating a cross-sectional view of a filter according to techniques of this disclosure. Filter 102 is an example filter configured to pass particles of a substance in a solution without also passing larger particles in a solution. In one example, filter 102 may be a single sheet of graphene with a thickness of 2 nm. In other examples, filter 102 may include multiple sheets of graphene to achieve a desired thickness. In other examples, filter 102 may include one or more Ultra Nanocrystalline Diamond membranes. It should be noted that although the apertures of filter 102 are illustrated as having a generally round shape, the actual shape of the apertures is affected based on the method used to manufacture filter 102. For example, in the case where filter 102 is a graphene sheet the edges of the aperture may be defined, in part, by the hexagonal carbon ring structure.

In the example illustrated FIG. 3, filter 102 is configured to pass objects with an effective diameter less than or equal to the effective diameter of the particles of glucose. As described above, a particle of glucose dissolved in blood at body temperature is assumed to have an effective diameter of approximately 0.72 nm. Thus, in order to pass objects with an effective diameter less than or equal to the effective diameter of the particles of glucose, filter 102 includes a plurality of apertures with a diameter slightly larger than 0.72 nm. In the example illustrated in FIG. 3, the diameter of apertures of filter 102 are nominally 0.74 nm. That is, the diameters of the apertures of filter 102 are approximately 2-3% larger than the effective diameter of glucose. It should be noted that the diameter of the apertures of filter 102 may further be increased to more efficiently pass glucose molecules. For example, the diameter of apertures of filter 102 may be within a range that is 2%-25% larger than the effective diameter particles of a substance to be isolated.

Further, it should be noted that the diameter of the apertures of filter 102 may be increased such that a particle of a substance to be isolated passes through filter 102 and a known larger size particle of a solution does not pass through filter 102. With reference to Table 1 above, the constituent of blood sequentially larger than glucose is sucrose, which may be assumed to have an effective diameter of 0.88 nm. Thus, in the example where glucose is to be isolated from blood the size of apertures of filter 102 may be increased to slightly smaller than 0.88 nm, such that sucrose does not pass through filter 102.

In the example illustrated in FIG. 3, the apertures of filter 102 have a nominal spacing of 2 nm. In principle, the flow rate will be proportional to the aperture density. As the aperture density increases (i.e., the nominal spacing decreases), the flow through the apertures of filter 102 may will increase, but may also become "turbulent," which may adversely affect the flow at a given pressure. Further, as the aperture density increases, the strength of filter 102 may be reduced, particularly when filter 102 is a single graphene sheet. A reduction in strength may, under some circumstances, cause filter 102 to rupture. Based on the flow and strength considerations a 2 nm center-to-center spacing between apertures is believed to be near optimum when filter 102 is a sheet of graphene. However, the nominal spacing between apertures of filter 102 may be readily increased or decreased based on desired flow rates and strength characteristics of filter 102.

Figure 4:
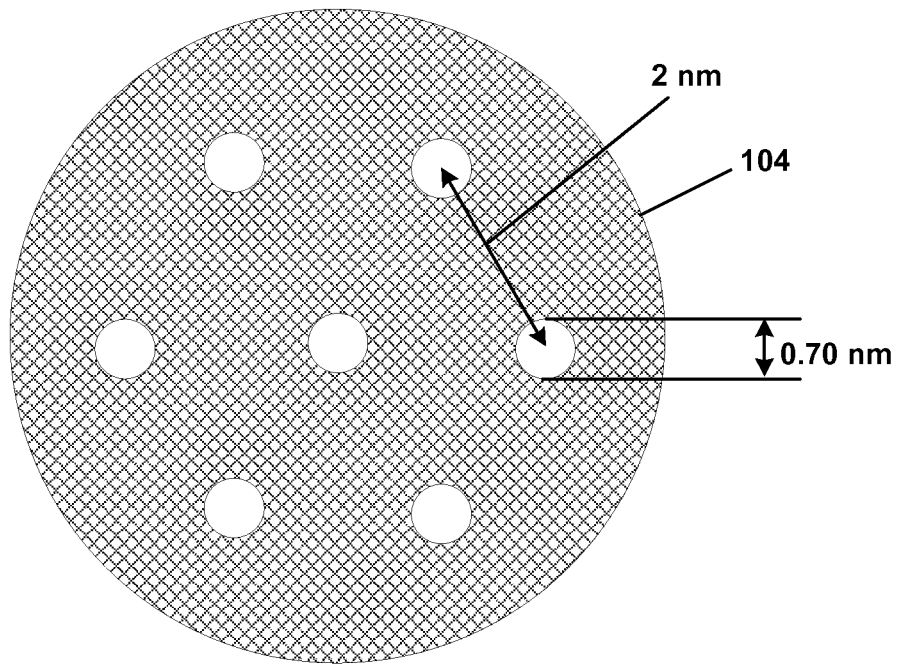
FIG. 4 is a conceptual diagram illustrating a cross-sectional view of a filter according to techniques of this disclosure.

FIG. 4 is a conceptual diagram illustrating a cross-sectional view of a filter according to techniques of this disclosure. Filter 104 may be of similar construction to filter 102 described above and for the sake of brevity construction details of filter 104 will not be described herein and reference is made to discussion of filter 102. In the example illustrated FIG. 4, filter 104 is configured to pass objects with an effective diameter less than the effective diameter of the particles of glucose, i.e. block glucose particles, while allowing smaller particles to pass through. As described above, a particle of glucose dissolved in blood at body temperature is assumed to have an effective diameter of approximately 0.72 nm. Thus, in order to pass objects with an effective diameter less than the effective diameter of the particles of glucose, filter 104 includes a plurality of apertures with a diameter slightly smaller than 0.72 nm. In the example illustrated in FIG. 3, the diameter of apertures of filter 104 are nominally 0.70 nm. That is, the diameters of the apertures of filter 104 are approximately 2-3% smaller than the effective diameter of glucose.

It should be noted that the diameter of the apertures of filter 104 may further be decreased. For example, the diameter of apertures of filter 104 may be within a range that is 2%-25% smaller than the effective diameter particles of a substance to be isolated. The diameter of the apertures of filter 104 may be decreased such that a particle of a substance to be isolated does not pass through filter 104 and a known smaller particle of a solution passes through filter 104. In some instances reducing the diameter of the apertures may increase the strength of filter 104. As illustrated in FIG. 4, the apertures of filter 104 have a nominal spacing of 2 nm. As discussed above with respect to filter 102, spacing of apertures can be determined based on a desired flow rate and a required level of strength. The spacing of the apertures of FIG. 4 may be determined based on similar characteristics. Further, the diameter of apertures of filter 104 may be determined based on similar characteristics.

Figure 5:
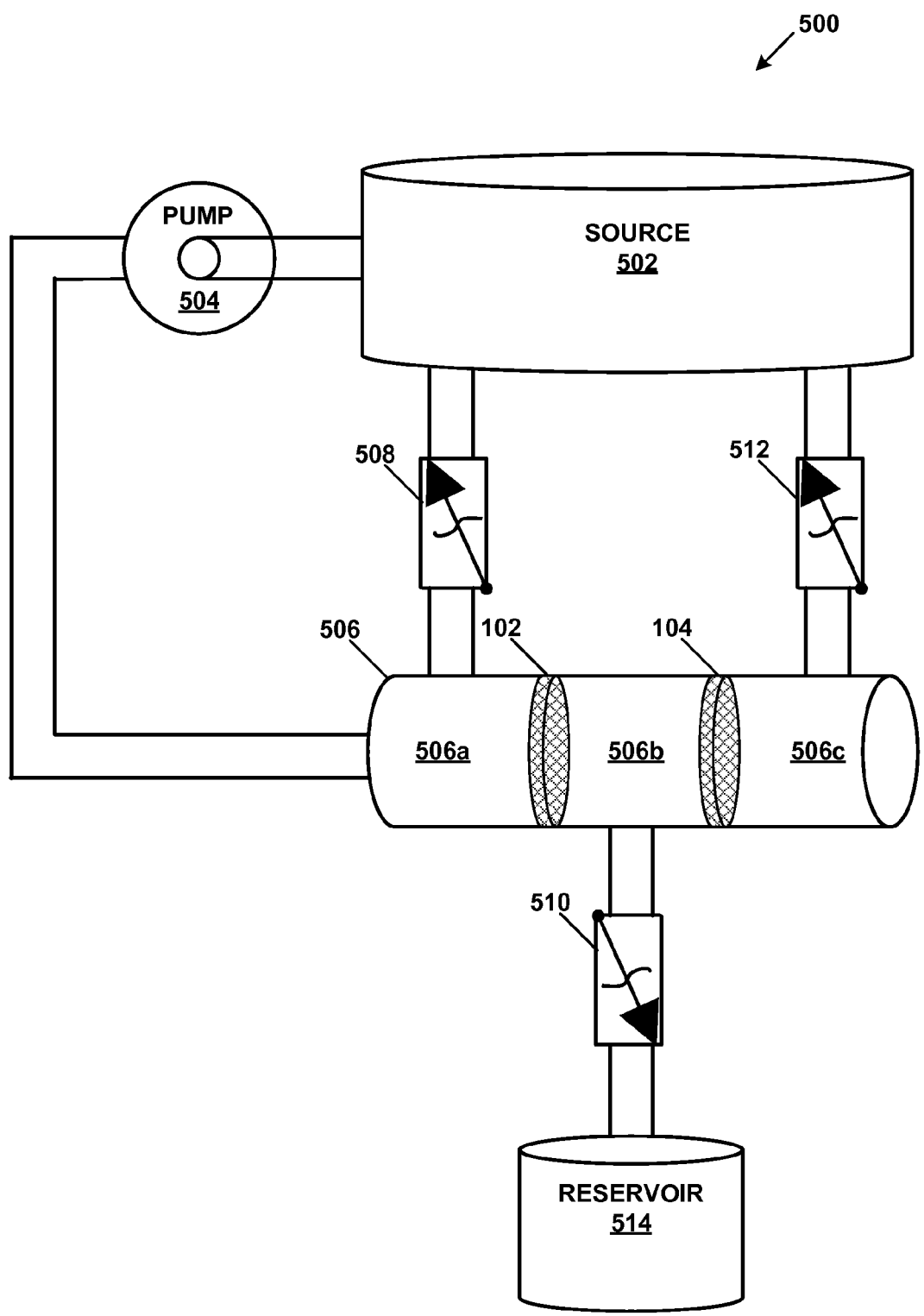
FIG. 5 is a conceptual diagram illustrating an example device for isolating a substance from a solution according to techniques of this disclosure.

FIG. 5 is a conceptual diagram illustrating an example device for isolating a substance from a solution according to techniques of this disclosure. As illustrated in FIG. 5, device 500 includes source 502, pump 504, chamber 506, pressure valve 508, pressure valve 510, pressure valve 512, and reservoir 514. Further, chamber 506 includes first section 506a, first filter 102, second section 506b, second filter 104, and third section 506c. Components of device 500 may be operably coupled as illustrated in FIG. 5.

In one example, components are connected using flexible tubes that are configured to accommodate moderate expansion of based on the volume of fluid in each section. For example, tubes may be constructed using known flexible materials, such as, rubber or plastic. Source 502 may be any container containing a solution from which a substance is to be isolated. In the example where glucose is to be isolated from blood, source 502 may be the circulatory system of a patient or an intermediate vessel containing blood drawn from a patient. Pump 504 is operably coupled to source 502 and is configured to circulate a solution from source 502 through chamber 506 and back to source 502. Pump 504 may be any type of electric, mechanical, or electromechanical pump configured to circulate a solution according to a desired flow rate. As a solution passes through chamber 506 a substance is isolated from a solution according to the general principles of two stage filtering described above with respect to FIG. 2.

As illustrated in FIG. 5, first section 506a of chamber 506 is operably coupled to pump 504, first filter 102, and pressure valve 508, which is in turn operably coupled to source 502. Pump 504 causes fluid to enter section 506a from the source 502. First filter 102 and pressure valve 508 determine which portions of solution (e.g., constituents of blood) flow into second section 506b of chamber 506 and which portions of solution circulate back to source 502. First filter 102 may be any of the example first filters described above. In the example where glucose is to be isolated from blood, first filter 102 may include a sheet of graphene including apertures sized and spaced according to the example illustrated in FIG. 3. Pressure valve 508 may be a one-way pressure release valve (also referred to as a pressure diode). Pressure valve 508 may be configured to have a pressure setting such that there is no uncontrolled pressure build-up in section 506a while solution is pumped from source 502 through first filter 102 at a given flow rate. Further, the pressure release setting of pressure release valve 508 may be set to achieve a steady-state operation based on desired flow rates of solution passing through filter 102 and solution circulating back to source 502. In the example where glucose is isolated from blood, pump 504, first filter 102, and pressure release valve 508 may be configured such that objects having a size less than or equal to the size of glucose enter second section 506b and objects have a size larger than the size of glucose circulate back to source 502, according to desired flow rates.

Objects that are able to pass through first filter 102 enter second section 506b of chamber 506. As illustrated in FIG. 5, second section 506b is operable coupled second filter 104 and pressure release valve 510. Second filter 104 may be any of the example second filters described above. In the example where glucose is to be isolated from blood, second filter 104 may include a sheet of graphene including apertures sized and spaced according to the example illustrated in FIG. 4. In this example, object having a size smaller than a glucose molecule are able to enter section 506c and subsequently return to source 502. Reservoir 514 is configured to receive objects that do not pass through filter 104, e.g., glucose molecules.

Thus, as a solution circulates through chamber 506 the substance to be isolated accumulates in reservoir 514. Pressure valves 510 and 512 may be configured such that there is no uncontrolled pressure build-up in sections 506b and 506c while solution is pumped from section 506b through second filter 104. Further, pressure release valves 510 and 512 may be configured to achieve a steady-state operation based on a desired rate of filtration. The amount of a substance in reservoir 514 may be measured in order to determine the amount of substance that has been isolated for a solution. In this manner, device 500 represents an example of a device configured to isolate a substance from a solution, wherein particles of the substance have an effective diameter that is within a range defined by effective diameters of a solution.

Figure 7:
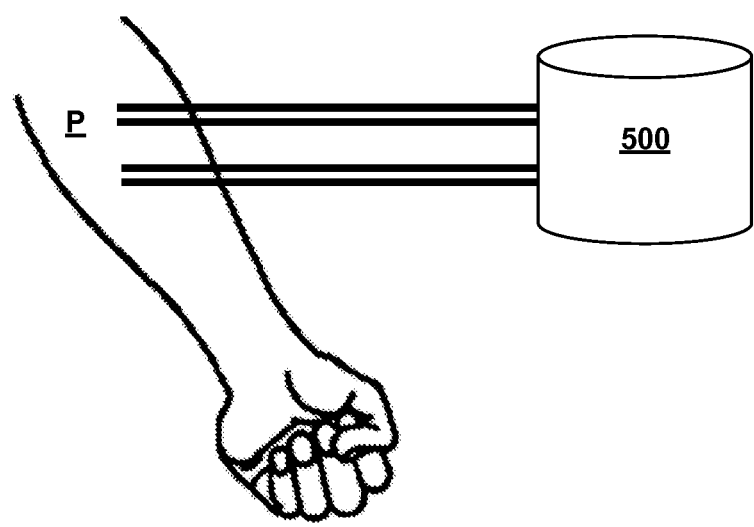
FIG. 7 is a conceptual diagram illustrating an example device for isolating a substance from blood affixed to a patient.

In some examples device 500 may be implemented as part of an external medical device or may be implemented as part of an implantable medical. FIG. 7 is a conceptual diagram illustrating an example device for isolating a substance from blood affixed to a patient. In the example, illustrated in FIG. 7 device 500 is an external medical device that is operably coupled to patient P. In this manner, device 500 is an example of a device configured to isolate a substance from blood, wherein particles of the substance have an effective diameter that is within a range defined by effective diameters of constituents of blood.

Figure 6:
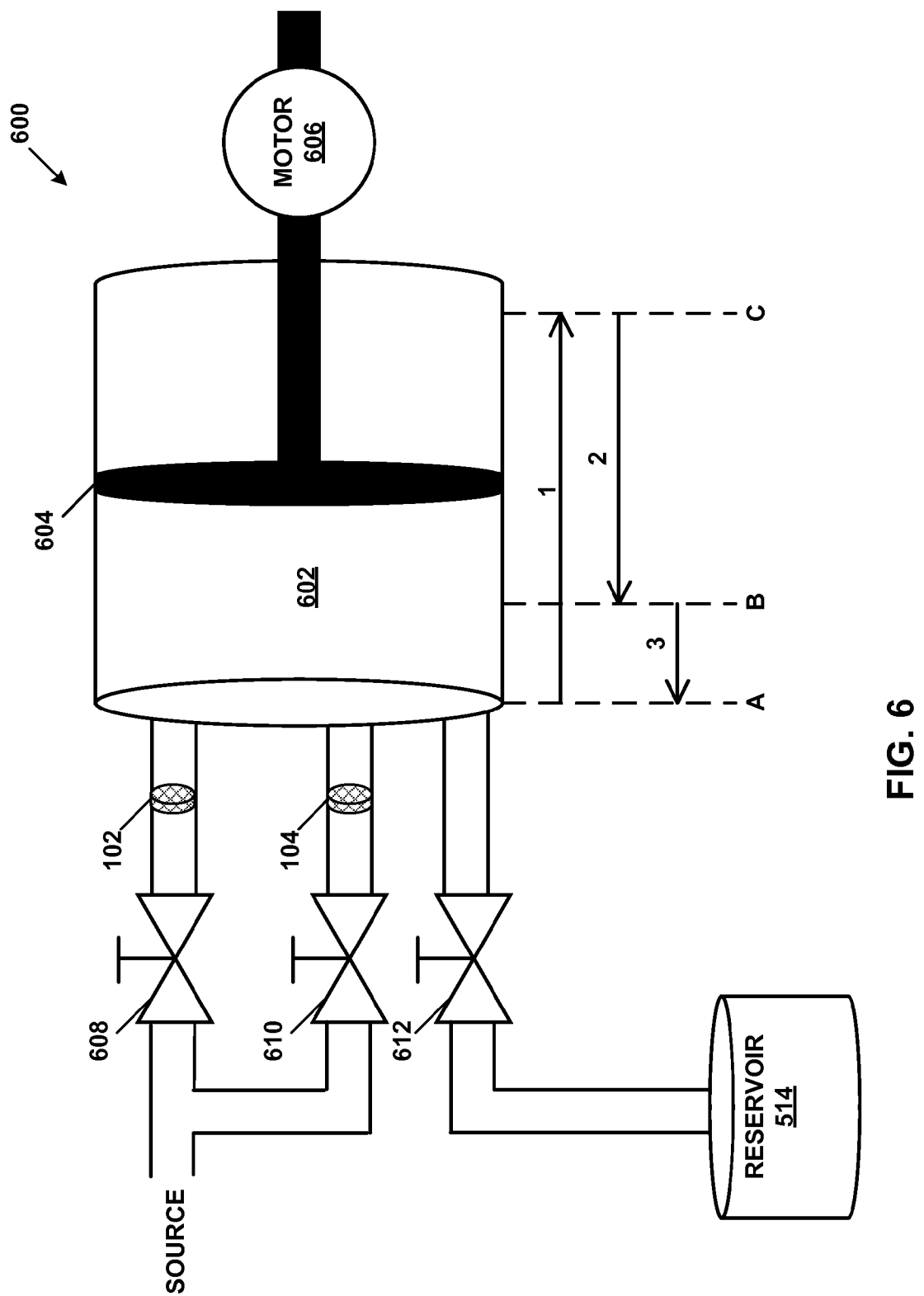
FIG. 6 is a conceptual diagram illustrating an example device for isolating a substance from a solution according to techniques of this disclosure.

FIG. 6 is a conceptual diagram illustrating an example device for isolating a substance from solution according to techniques of this disclosure. Device 600 may be configured to draw a solution from a source and return the solution to a source, wherein the returned solution does not include an isolated substance. A source may be any container containing a solution from which a substance is to be isolated. In the example where glucose is to be isolated from blood, source may be the circulatory system of a patient or an intermediate vessel containing blood drawn from a patient. Device 600 is configured to operate according to a reversible mechanical cycle.

As illustrated in FIG. 6, device 600 includes first filter 102, second filter 104, cylinder 602, piston 604, motor 606, valve 608, valve 610, valve 612, and reservoir 510. First filter 102 may be any of the example first filters described above. In the example where glucose is to be isolated from blood, first filter 102 may include a sheet of graphene including apertures sized and spaced according to the example illustrated in FIG. 3. Second filter 104 may be any of the example second filters described above. In the example where glucose is to be isolated from blood, second filter 104 may include a sheet of graphene including apertures sized and spaced according to the example illustrated in FIG. 4. As illustrated in FIG. 6, components of device are operably coupled. In one example, cylinder 602 and sections operably coupling elements may be constructed of rigid material.

As illustrated in FIG. 6, piston 604 is disposed in cylinder 602 and operably coupled to motor 606. Motor 606 is configured to cause head of piston 604 to move between position A of cylinder 602 to position C of cylinder 602 and back. Motor 606 may be any type of translation motor that causes piston 604 to move from position A to position C in a reversible manner. Valve 608, valve 610, and valve 612 are controllable valves that may opened or closed. Valve 608, valve 610, and valve 612 may be configured such that they may be opened or closed using an electrical signal. In one example, the electrical signal may be generated using a general purpose computer configured to operate according to techniques described in this disclosure. As described in detail below, device 600 is configured such that valves 608, valve 610, and valve 612 are opened and closed as piston 604 completes moves through cylinder 602 in a reversible manner such that a substance may be isolated from a solution.

Device 600 may be configured such that in an initial operational state head of piston 604 is in position A with valve 608 open and valves 610 and 612 closed. Motor 606 may cause head of piston 604 to move from position A to position C (1). Thereby drawing a solution from a source through first filter 102 and into cylinder 602. In the example where glucose is the substance to be isolated from blood first filter 102 may be configured such that objects having a size less than or equal to the size of glucose enter cylinder 602 and objects have a size larger than the size of glucose remain on the side of first filter 102 opposite cylinder 602. After cylinder 602 is filled (i.e., head of piston 602 reaches position C), valve 608 may be closed and valve 610 may be open while valve 612 remains closed. Motor 606 then causes head of piston 604 to move from position C to position B (2). Thereby causing contents of cylinder 602 to flow through second filter 104 to source. In the example where glucose is the substance to be isolated from blood second filter 104 may be configured such that objects having a size less than the size of glucose return to source and glucose remains between the opposite side of filter 104 and position B.

When head of piston 604 reaches position B, valve 610 may be closed and valve 612 may be opened and motor 606 may cause head of piston 604 to move from position B to position A. Thereby causing particles that were able to pass through first filter 102 but not able to pass through second filter 104 to be isolated in reservoir 514. As described above with respect to FIG. 5, the amount of a substance in reservoir 514 may be measured in order to determine the amount of substance that has been isolated for a solution. When the head of piston 604 returns to position A, valve 612 may be closed and valve 608 may be opened. Thereby return device 600 to the initial operation state described above.

The process of respectively opening and closing the valve 608, valve 610, and valve 612 as piston 604 moves from positions A to C to B to A may be repeated as necessary to continually isolate a substance in reservoir. Source should be continuously replenished and mixed, as fluid enters from the source through valve 608 and returns to the source through valve 610. In should be noted that position B may be adjusted during an initial calibration of device 600 so that the cylinder 602 contains few or no small objects (e.g. smaller than a substance to be isolated) before valve 610 is closed and valve 612 is opened and head of piston 604 is moved from position B to position A. In this manner, device 600 represents an example of a system configured to isolate a substance from a solution, wherein particles of the substance have an effective diameter that is within a range defined by effective diameters of a solution.

Figure 8:
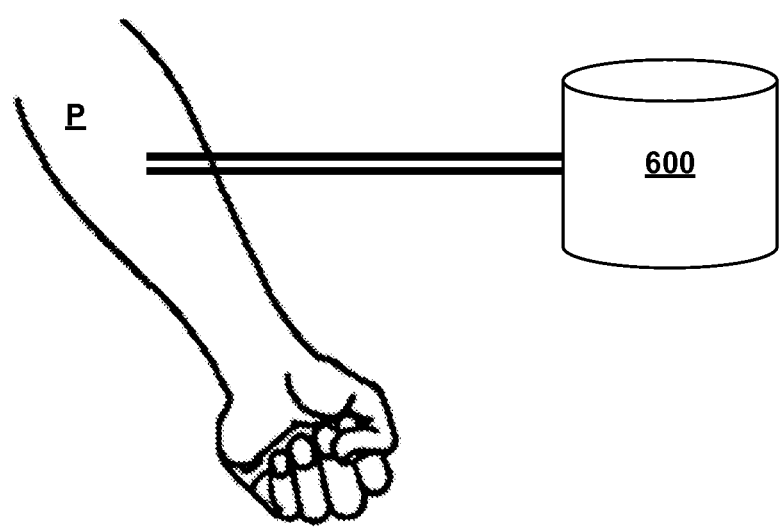
FIG. 8 is a conceptual diagram illustrating an example device for isolating a substance from blood affixed to a patient.

In some examples device 600 may be implemented as part of an external medical device or may be implemented as part of an implantable medical. FIG. 8 is a conceptual diagram illustrating an example device for isolating a substance from blood affixed to a patient. In the example illustrated in FIG. 8, device 600 is an external medical device that is operably coupled to patient P. In this manner, device 600 is an example of a device configured to isolate a substance from blood, wherein particles of the substance have an effective diameter that is within a range defined by effective diameters of constituents of blood.

Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. The upper and lower limits of these smaller ranges which may independently be included in the smaller ranges is also encompassed within the disclosure, subject to any specifically excluded limit in the stated range. Where the stated range includes one or both of the limits, ranges excluding either both of those included limits are also included in the disclosure.

Unless defined otherwise, all technical and scientific terms used herein have the same meaning as commonly understood by one of ordinary skill in the art to which this disclosure belong. Although any methods and materials similar or equivalent to those described herein can also be used in the practice or testing of the disclosure, the preferred methods and materials are now described. All patents and publications mentioned herein, including those cited in the Background of the application, are hereby incorporated by reference to disclose and described the methods and/or materials in connection with which the publications are cited.

The publications discussed herein are provided solely for their disclosure prior to the filing date of the present application. Nothing herein is to be construed as an admission that the present disclosure are not entitled to antedate such publication by virtue of prior invention. Further, the dates of publication provided may be different from the actual publication dates which may need to be independently confirmed.

Other embodiments of the present disclosure are possible. Although the description above contains much specificity, these should not be construed as limiting the scope of the disclosure, but as merely providing illustrations of some of the presently preferred embodiments of this disclosure. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form various embodiments. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

The foregoing description of various preferred embodiments of the disclosure have been presented for purposes of illustration and description. It is not intended to be exhaustive or to limit the disclosure to the precise embodiments, and obviously many modifications and variations are possible in light of the above teaching. The example embodiments, as described above, were chosen and described in order to best explain the principles of the disclosure and its practical application to thereby enable others skilled in the art to best utilize the disclosure in various embodiments and with various modifications as are suited to the particular use contemplated. It is intended that the scope of the disclosure be defined by the claims appended hereto.

Various examples have been described. These and other examples are within the scope of the following claims.

What is claimed is:

1. A method for isolating glucose from blood, the method comprising:
   regulating the flow of the blood through a first sheet of graphene and a second sheet of graphene,
   wherein the first sheet of graphene comprises a first plurality of apertures with an effective diameter that allows passage of glucose across the first sheet of graphene; and
   wherein the second sheet of graphene comprises a second plurality of apertures with an effective diameter less than the effective diameter of glucose.

2. The method of claim 1, wherein the first plurality of apertures comprises apertures with a nominal diameter of at least 0.74 nanometers and the second plurality of apertures comprises apertures with a nominal diameter less than 0.70 nanometers.

3. The method of claim 2, wherein the first plurality of apertures comprises apertures that are nominally spaced 2 nanometers center-to-center.

4. The method of claim 3, wherein the second plurality of apertures comprises apertures that are nominally spaced 2 nanometers center-to-center.

5. The method of claim 2, wherein regulating the flow of the blood through the first sheet of graphene and the second sheet of graphene includes circulating blood from a source through a conduit system.

6. The method of claim 2, wherein regulating the flow of the blood through the first sheet of graphene and the second sheet of graphene includes using a reversible cycle.

7. The method of claim 5, wherein said regulation is with a device that comprises a plurality of pressure release valves configured to regulate the flow of the blood from the conduit system to the source.

8. The method of claim 6, wherein regulating the flow of the blood through the first sheet of graphene and the second sheet of graphene includes using a mechanical system comprising a piston disposed within a cylinder, wherein the piston is configured to circulate blood from a source through the cylinder.

9. The method of claim 8, wherein the mechanical system further includes a plurality of controllable valves, and wherein isolating the glucose using the reversible cycle includes drawing blood from the source through the first sheet of graphene and into the cylinder.

10. The method of claim 9, wherein isolating the glucose using the reversible cycle further includes returning blood from the cylinder to the source through the second sheet of graphene.

11. The method of claim 1, wherein the first plurality of apertures is approximately 2% to 25% larger than the effective diameter of glucose.

12. The method of claim 1, wherein the second plurality of apertures is approximately 2% to 25% smaller than the effective diameter of glucose.

13. The method of claim 1, wherein the diameter of the first plurality of apertures and the diameter of the second plurality of apertures differ by about 0.04 nanometers.

14. The method of claim 5, wherein the conduit system is a two stage bypass filter.

15. The method of claim 1, wherein the first sheet of graphene and the second sheet of graphene are configured in a medical device.

16. The method of claim 15, wherein the medical device is an implantable medical device.

17. The method of claim 1, wherein the first sheet of graphene, the second sheet of graphene or both are coupled with one or more additional sheets of graphene to form multiple sheet graphene membranes.

18. The method of claim 1, wherein the first sheet of graphene, the second sheet of graphene or both are coupled with one or more diamond membranes.

19. The method of claim 1, further comprising returning the blood that flowed through the first sheet of graphene and the second sheet of graphene to its source.

20. The method of claim 1, wherein the first plurality of apertures comprises apertures that are approximately 2% to 25% larger than the effective diameter of glucose, and wherein the second plurality of apertures comprises apertures that are approximately 2% to 25% smaller than the effective diameter of glucose.

21. The method of claim 1, wherein the first plurality of apertures comprises apertures that are approximately 2% larger than the effective diameter of glucose, and wherein the second plurality of apertures comprises apertures that are approximately 2% smaller than the effective diameter of glucose.

22. The method of claim 1, wherein the first plurality of apertures comprises apertures with a nominal diameter of approximately 0.74 nm, and wherein the second plurality of apertures comprises apertures with a nominal diameter of approximately 0.70 nm.

23. A method for isolating glucose from blood, the method comprising:
passing blood through a first sheet of graphene and a second sheet of graphene,
wherein the first sheet of graphene comprises a first plurality of apertures with a nominal diameter of approximately 0.74 nm, and
wherein the second sheet of graphene comprises a second plurality of apertures with a nominal diameter of approximately 0.70 nm,
to thereby isolate the glucose from the blood.

24. The method of claim 23, wherein the first sheet of graphene consists of a first plurality of apertures with a nominal diameter of approximately 0.74 nm, and wherein the second sheet of graphene consists of a second plurality of apertures with a nominal diameter of approximately 0.70 nm.

25. A method for isolating glucose from blood, the method comprising:
passing blood through a first sheet of graphene and a second sheet of graphene,
wherein the first sheet of graphene comprises a first plurality of apertures with a nominal diameter of at least 0.74 nm, and
wherein the second sheet of graphene comprises a second plurality of apertures with a nominal diameter of less than 0.70 nm,
to thereby isolate the glucose from the blood.

26. The method of claim 21, wherein the first plurality of apertures have a nominal diameter of from 0.74 nm to 0.9 nm.

27. The method of claim 21, wherein the second plurality of apertures have a nominal diameter of from 0.54 nm to 0.7 nm.

* * * * *